United States Patent
Beier et al.

(12)

(10) Patent No.: US 6,465,194 B2
(45) Date of Patent: Oct. 15, 2002

(54) MONOCLONAL ANTIBODIES TO 4,4'-DINITROCARBANILIDE AND A METHOD FOR ANALYZING FOR THE DRUG NICARBAZIN

(75) Inventors: Ross C. Beier, College Station, TX (US); Larry H. Stanker, Livermore, CA (US); Colin R. Young, College Station, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 39 days.

(21) Appl. No.: 09/726,186

(22) Filed: Nov. 29, 2000

(65) Prior Publication Data

US 2001/0039332 A1 Nov. 8, 2001

Related U.S. Application Data

(60) Provisional application No. 60/168,117, filed on Nov. 30, 1999.
(51) Int. Cl.[7] .............................................. G01N 33/53
(52) U.S. Cl. ...................... 435/7.1; 435/7.93; 435/7.94; 435/971; 435/975; 436/518; 436/543; 436/547; 436/548; 436/86; 436/815; 530/388.1
(58) Field of Search .................... 435/7.1, 7.93, 435/7.94, 971, 975; 436/518, 543, 547, 548, 86, 815; 530/388.1

(56) References Cited

PUBLICATIONS

Beier et al., Analytica Chimica Acta. vol. 376, pp. 139–143, 1998.*

Wong, Jennifer M., et al., "Method for the Analysis of 4–Nitrophenol and Parathion in Soil Using Supercritical Fluid Extraction and Immunoassay", *J. Agric. Food Chem.*, 1991, 39, pp. 1802–1807.

Xaio Li, Qing, et al., "Development of Enzyme–Linked Immonosorbent Assays for 4–Nitrophenol and Substituted 4–Nitrophenois", *J. Agic. Food Chem.*, 1991, 39, pp. 1685–1692.

\* cited by examiner

*Primary Examiner*—Bao-Thuy L. Nguyen
(74) *Attorney, Agent, or Firm*—M. Howard Silverstein; Randall E. Deck; John D. Fado

(57) ABSTRACT

Hybridoma cell lines have been generated which produce and secrete monoclonal antibodies which selectively bind to 4,4'-dinitrocarbanilide (DNC), the active agent of nicarbazin. These hybridomas may be obtained by using as an immunization agent or immunogen, p-nitroaniline which has been conjugated to an immunogenic carrier. DNC in biological samples may be detected and quantified by contacting the sample with the antibodies to form a DNC/antibody immunocomplex when DNC is present, which immunocomplex may then be detected. The monoclonal antibodies also may be incorporated into kits for the detection and quantification of DNC and/or nicarbazin.

18 Claims, 1 Drawing Sheet ial chromatography with UV detection

MONOCLONAL ANTIBODIES TO 4,4'-DINITROCARBANILIDE AND A METHOD FOR ANALYZING FOR THE DRUG NICARBAZIN

CROSS REFERENCE TO RELATED APPLICATION

This application hereby claims the benefit of U.S. provisional application No. 60/168,117, filed on Nov. 30, 1999, the contents of which are incorporated by reference herein.

BACKGROUND OF THE INVENTION

1. Field of the Invention

This invention relates to hybridoma cell lines and monoclonal antibodies produced therefrom which may be used to detect nicarbazin.

2. Description of the Prior Art

Nicarbazin is a feed additive used to prevent outbreaks of cecal and intestinal coccidiosis in poultry, and is composed of an equimolar complex of 4,4'-dinitrocarbanilide (DNC) and 2-hydroxy-4,6-dimethylpyrimidine (HDP). Coccidiosis causes economic losses to the poultry industry [Long (Ed.), The Biology of the Coccidia, University Park Press, Baltimore, Md., 1982]. Nicarbazin was the first agent found to give satisfactory control of coccidiosis in broiler production (Cuckler et al., 1955, Science, 122:244–245; and Cuckler et al., 1956, Poult. Sci., 35:98–109). Nicarbazin also is used to increase the rate of weight gain. The complex, DNC-HDP, is ten times more potent in the control of Eimeria tenella, the primary coccidia cecal pathogen, as is DNC by itself. However, HDP when used alone was observed to have no anticoccidial activity (Cuckler et al., 1955, ibid). It was proposed that ultrafine crystals that are obtained as a result of complex formation allows for better dissolution of DNC resulting in improved anticoccidial activity (Rogers et al., 1983, Science, 222:630–632). Chickens also excrete DNC more slowly than HDP (Porter and Gilfilan, 1955, Poultry Sci., 34:995–1001). The U.S. Food and Drug Administration (FDA) has established a withdrawal period for nicarbazin of 4 days with a tolerance of 4 ppm (Code of Federal Regulations, 21 CFR 556.445). The Food Safety and Inspection Service (FSIS) uses high performance liquid chromatography (HPLC) with UV detection to analyze for DNC (Anon, in Analytical Chemistry Laboratory Guidebook: Residue Chemistry, USDA-FSIS Science and Technology Program, Washington, D.C., 1991, p. NIC-1). The FSIS method, as well as other published methods, use a variety of organic solvents (e.g., ethyl acetate, acetonitrile, hexane, dimethylformamide, and methanol) for extraction and other steps used in the analyses of DNC (Michielli and Downing, Jr., 1974, J. Agric. Food Chem., 22:449–452; Wood, Jr. and Downing, 1980, J. Agric. Food Chem., 28:452–454; Macy and Loh, 1984, J. Assoc. Off. Anal. Chem., 67:1115–1117; Parks, 1988, J. Assoc. Off. Anal. Chem., 71:778–780; and Lewis et al., 1989, J. Assoc. Off. Anal. Chem., 72:577–581); matrix solid-phase dispersion extraction followed by liquid chromatographic determination of DNC also has been used (Schenck et al., 1992, J. AOAC Intern., 75:659–662). All of these methods are time-consuming and result in generating substantial organic solvent wastes.

Our laboratory has had a long-term interest in developing monoclonal antibodies and immunochemical methods for the determination of all regularly used coccidiostats in poultry production. Detection methods based on immunoassays can greatly increase the rate of sample through-put, and allow the screening of increased numbers of samples without increasing the cost of analysis.

Our original approach to the production of monoclonal antibodies (MAbs) to DNC was to make a hapten from the drug DNC and use it for immunization. This was accomplished by using DNC and 4-hydrazinobenzoic acid to form the hydrazone. The hydrazone was then coupled to a carrier protein, keyhole limpet hemocyanin (KLH), using 1-ethyl-3-(3-dimethylamino-propyl)carbodiimide HCl (EDC), and mice were immunized with the conjugate. Cell fusions were performed and screened for antibody activity. Antibodies to the hapten were obtained, but these were never observed to compete with "free" DNC.

SUMMARY OF THE INVENTION

We have now discovered hybridoma cell lines which produce and secrete monoclonal antibodies which selectively bind to 4,4'-dinitrocarbanilide (DNC). We have unexpectedly found that these hybridomas may be obtained by using as an immunization agent or immunogen, p-nitroaniline which has been conjugated to an immunogenic carrier. DNC in biological samples may be detected and quantified by contacting the sample with the antibodies to form a DNC/antibody immunocomplex when DNC is present, which immunocomplex may then be detected. The monoclonal antibodies also may be incorporated into kits for the detection and quantification of DNC and/or nicarbazin.

It is an object of this invention to provide hybridoma cell lines that produce and secrete high affinity monoclonal antibodies which selectively bind to DNC.

Another object of this invention is to provide immunoassay methods for the measurement of DNC and/or nicarbazin in biological samples.

A further object is to provide kits useful for the assay of DNC and/or nicarbazin which include the monoclonal antibodies described herein.

Yet another object is to provide an immunization agent which may be used to produce hybridoma cell lines that produce and secrete high affinity monoclonal antibodies which selectively bind to DNC.

Other objects and advantages of this invention will become readily apparent from the ensuing description.

DETAILED DESCRIPTION OF THE INVENTION

Figure 1:
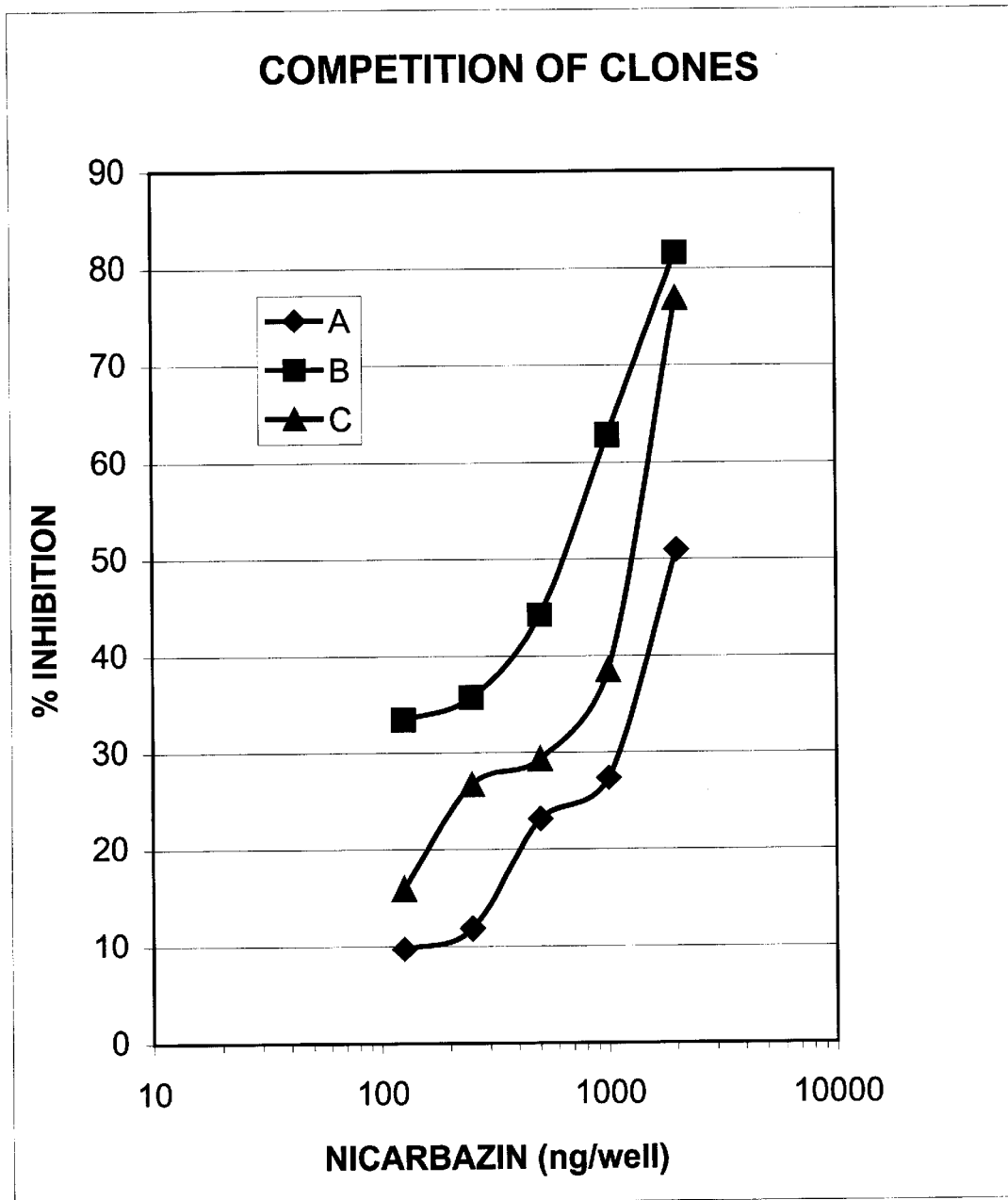
FIG. 1 shows the competitive inhibition ELISA standard curves for three of the anti-carbanilide antibodies of the invention using free nicarbazin as a competitor. The three clones shown are A=PNA-S2 6/3-56(2)-3-1-5, B=PNA-S2 6/3-56(1)-1-5-1, and C=PNA-S2 6/3-56(1)-1-5-2.

In accordance with this invention, we have created hybridoma cell lines that produce monoclonal antibodies that bind 4,4'-dinitrocarbanilide (DNC) and are effective for detecting and quantifying levels of the coccidiostat nicarbazin. We have unexpectedly discovered that by use of a novel immunogen, monoclonal antibodies may be produced which possess improved specificity and increased affinity for DNC. The antibodies of this invention may be used to rapidly and accurately detect and quantify DNC and/or nicarbazin, providing an indicator of the level of these compounds in biological samples.

Traditionally, preparation of hybridomas may be accomplished using conventional techniques such as described by Kohler and Milstein [Nature, 256:495–497 (1975)], Koprowski et al. [U.S. Pat. No. 4,196,265], Wands [U.S. Pat. No. 4,271,145], or Stanker et al. [U.S. Pat. No. 5,466,784], the contents of each of which are incorporated by reference herein. Briefly, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen.

Often, the compound of interest is a relatively small molecule, and hence is itself incapable or only poorly capable of stimulating the immune system to produce antibodies. To render such compounds immunogenic, they are generally conjugated to an immunogenic carrier in such a manner that the resultant immunogen is capable of stimulating the immune system of an animal to produce specific antibodies that are capable of binding the unconjugated compound. Application of this traditional protocol for the generation of monoclonal antibodies to a small compound such as DNC, would logically dictate an immunogen prepared by conjugation of DNC to a carrier protein. However, in a departure from established practice, we describe here the preparation of monoclonal antibodies using significantly different, novel immunogens.

The method of preparing the hybridomas comprises the following steps:

Immunogen. The immunization agent of this invention is not constructed from DNC, but from p-nitroaniline. The structures of DNC and p-nitroaniline are shown in formulas I and II, respectively:

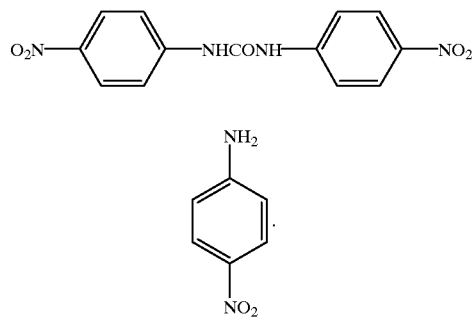

The immunization agent is prepared by covalently conjugating an immunogenic carrier to p-nitroaniline. Immunogenic carriers are defined herein as any compound to which the haptens may be attached to render them immunogenic. Suitable carriers are well known and may be readily determined by the practitioner skilled in the art. Without being limited thereto, preferred carriers include proteins such as keyhole limpet hemocyanin (KLH), bovine serum albumin (BSA), ovalbumin, glucose oxidase, and human thyroglobulin.

The immunogenic carrier may be conjugated to the p-nitroaniline molecule with a crosslinking agent or spacer. In accordance with the preferred embodiment, the immunogen is created by combining a crosslinking to the free amine moiety of p-nitroaniline through an amide linkage. As described in greater detail in Example 1, in a particularly preferred embodiment, the carrier protein is conjugated to p-nitroaniline modified by reaction with an amine reactive bifunctional crosslinking agent, such as succinic acid or other dicarboxylic acid. Other crosslinking agents suitable for conjugating a carrier protein and p-nitroaniline through the hapten's amine group, include but are not limited to dicarboxylic acids such as glutaric acid or adipic acid, or amino carboxylic acids such as primary, secondary, tertiary or higher amino acids. Immunogens prepared by conjugation of p-nitroaniline to a carrier protein through a crosslinking agent may be generally described by the formula (III):

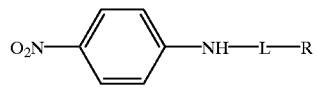

wherein L refers to the crosslinking agent and R is a carrier protein.

Immunization. To generate antibody-producing splenocytes or lymphocytes, an immunizing preparation comprising the p-nitroaniline-carrier complex is injected into an immunologically competent animal. The preparation may also contain other proteins, although pure or partially pure compositions of the conjugate in a pharmaceutically acceptable carrier are preferred.

Without being limited thereto, rats and particularly mice are preferred animals for immunization because of ease of handling. Preparation of hybridomas using splenocytes from these animals fused to a variety of myeloma cell lines have been reported by many investigators.

Inoculations of the animal can be by various routes. A series of three inoculations, generally at two week intervals, with a composition of the complex in isotonic saline with RIBI adjuvant (Immunochem Research, Inc., Hamilton, Mont.) elicits good antibody response, and is preferred. The skilled practitioner will recognize that other routes of administration, immunization schedules, and carriers or adjuvants may be used.

Hybridization. Splenocytes or lymphocytes recovered from the immunized animal are fused with continuously replicating tumor cells, such as myeloma or lymphoma cells, cultured, and hybridoma cells selected. Many continuously replicating tumor cell lines are available which may be used as fusion partners with the splenocytes. Without being limited thereto, preferred myeloma cells include P3-NS1-K653, and particularly SP2/0.

Fusion and culture of the cells can be performed using conventional techniques. In accordance with one well-known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to DNC or nicarbazin. In accordance with the preferred embodiment, the supernatants are screened using a modification of the direct-binding ELISA (db-ELISA). In this embodiment, solid substrates, such as beads or the wells of a microtiter plate, which have been coated with DNC or nicarbazin, are used to bind anti-DNC antibody in the supernatants, and bound antibody is then detected. Surprisingly, we have found that despite the small size of the DNC hapten molecule, it remains effective for binding the anti-DNC antibody when it is coated on the solid substrate. In contrast, p-nitroaniline-carrier complexes and DNC-carrier complexes are ineffective for binding the antibody when coated on a solid substrate at standard pH conditions of approximately 7.75. Adsorption of DNC onto the substrate may be achieved by dissolving DNC or nicarbazin in a solvent, contacting the solution with the support, and washing. Methanol is a preferred solvent for use herein, particularly when combined with buffer as described in the Examples. Alternatively, the db-ELISA may be conducted using solid substrate coated with a p-nitroaniline-carrier protein, such as described above for the immunogen with a different carrier protein, but only when using a lower pH (i.e., approximately 7.4) for the assay than used with DNC or nicarbazin coated plates. For instance, solid substrates coated with BSA-PNA-C in carbonate buffer, pH9, can be used to bind anti-DNC antibody in the supernatants using standard assay buffer at approximately pH 7.4.

Following contact of the supernatant culture fluid with the DNC-coated substrate, detection of bound antibody may be accomplished by addition of enzyme-labeled anti-immunoglobulin antibodies followed by enzyme substrate. While a variety of enzyme/substrate labels may be used, horse radish peroxidase and its substrate, 2,2'-azinobis-3-ethylbenthiazolinesulfonic acid (ABTS) are preferred. In the alternative, it is understood that the supernatants also may be screened using non-enzyme labels, such as radiolabels or chromophores, in related solid-phase immunosorbent techniques such as RIA, FIA.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas also may be screened to select for those producing antibodies having a high affinity for DNC or nicarbazin. Affinity may be measured using solid phase immunoassays such as ELISA or RIA. In the preferred embodiment, affinity is measured by competitive indirect ELISA as described in the Examples, and is conducted at a final antibody concentration (dilution from the tissue culture supernatant) to give 50% of maximal binding to a DNC or nicarbazin coated substrate or assay well (i.e., the concentration of the antibody that results in 50% of the plateau activity in direct binding ELISA). In accordance with this embodiment, the antibody containing supernatant is added to a DNC or nicarbazin coated substrate such as the wells of a microtiter plate (prepared as described above), together with a range of concentrations of free DNC or nicarbazin as a competitor. Because the DNC in nicarbazin is very insoluble in water, it was necessary to develop a solvent system which was not only effective for solubilizing the drug, but which was still suitable for use in an immunoassay. We have found that acetonitrile (ACN) or methanol, preferably in combination with N,N-dimethylformamide (DMF), are effective solvents for DNC, and formulations of these solvents are used to dissolve the DNC or nicarbazin and prepare standard solutions. In the preferred embodiment, for preparation of standard solutions of DNC, suitable concentrations of ACN (or methanol) may vary between about 1–50% with about 0–15% DMF (1–15% when using methanol). However, at the higher concentrations within these ranges (i.e., typically greater than about 20% ACN or methanol, and about 5% DMF), these solvents are unsuitable for use in an ELISA or RIA. If necessary, prior to addition of anti-DNC antibody or hybridoma to the assay medium, the medium should therefore be diluted with a suitable buffer such as described in the Examples to an overall concentration of between about 1–20% ACN (or methanol) and about 0–5% DMF.

Following incubation with the anti-DNC antibody or the hybridoma culture supernatant and washing, bound antibody in the wells is determined in the same manner as the db-ELISA. Percent inhibition may be calculated as $(1-B/B_o) \times 100$, where B is the optical density (OD) of a well with a competitor and $B_o$ is the mean OD of the wells without competitor (control). The relative affinity of the antibodies may be accurately measured as the concentration of free DNC (or nicarbazin) added to the wells that results in at least 20% inhibition ($IC_{20}$) of control activity. However, for greater accuracy, the affinity may be alternatively measured at 50% inhibition ($IC_{50}$).

Once hybridomas producing and secreting the desired anti-DNC antibodies are identified, large quantities of the antibodies may be produced in tissue culture using well-known techniques. Alternatively, antibodies may be produced within host animals, such as by ascites formation in syngenic mice. Monoclonal antibodies so produced may be purified, for example, by affinity chromatography on a protein A or G resin, or using DNC bound to a resin.

The monoclonal antibodies produced in accordance with this invention possess high affinity for DNC and nicarbazin, allowing the rapid determination of these agents at low levels. As described in detail in Example 2, when the sensitivity was measured at a high standard of accuracy ($IC_{50}$) by competitive inhibition ELISA, the detection limits of the antibodies for DNC ranged from 462 to 1555 ng.

The antibodies may be used to detect and/or quantify DNC or nicarbazin in unknown samples using a variety of conventional immunosorbent assays including but not limited to RIA, FIA or ELISA. A competitive inhibition ELISA similar to that used to screen the hybridomas is preferred. In this assay, a sample to be analyzed is incubated with the monoclonal antibody for DNC and a solid substrate coated with DNC or nicarbazin. After incubation, the solid phase is drained and washed, and bound antibody on the substrate is detected and percent inhibition calculated as described earlier. The concentration of DNC or nicarbazin in the sample may then be determined by reference to a standard curve constructed from assays using known levels of DNC or nicarbazin.

In one alternative embodiment, DNC or nicarbazin may be determined by a competition ELISA such as described in Brandon et al. (U.S. Pat. No. 5,053,327, the contents of which are incorporated by reference herein) using the monoclonal antibody of the invention attached to a solid support. For example, the anti-DNC antibody may be immobilized on a solid support such as a bead or microtiter well. The unknown sample to be analyzed (or analytical standards of DNC or nicarbazin) are then added with enzyme or radio-labeled DNC, and the amount of labeled DNC bound to the antibody is measured, using a substrate when the label is an enzyme. The amount of DNC or nicarbazin in the sample is inversely proportional to the amount of bound labeled DNC. In another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having DNC or nicarbazin attached thereto.

Determination of DNC or nicarbazin in a variety of feeds or biological samples, including animal tissue and animal fluids such as serum, may be conducted using the above-described assays with minimal sample preparation and using simple extraction procedures. For the analysis of tissue samples, the tissue may be homogenized in buffer, such as Tris-HCl, centrifuged, and the liquid phase recovered and used directly in the immunoassay. Although any animal tissue may be analyzed, the assay is particularly valuable for the determination of DNC or nicarbazin in meats. Tissue for analysis in accordance with the invention may originate from virtually any animal. Without being limited thereto, the assays are preferably used for the analysis of feeds and tissue samples and meats from domestic animals, particularly poultry.

Another application of the monoclonal antibodies is affinity purification of DNC. The antibodies may be bound to a matrix, column, or other support using well-known techniques and used to recover or remove DNC from any desired material. Alternatively, the monoclonal antibodies may be incorporated into sensors such as solid phase electronic devices for detection of DNC or nicarbazin in sample materials.

The following examples are intended only to further illustrate the invention and are not intended to limit the scope of the invention which is defined by the claims.

EXAMPLE 1

Immunogen Production

Synthetic Method for p-nitrosuccinanilic Acid.

p-Nitroaniline (PNA) (0.1 g, 0.724 mmol) and succinic anhydride (SA) (0.29 g, 2.898 mmol) were dissolved in ethyl acetate (EtOAc) (4 mL). Slight warming was required to dissolve both PNA and SA. The reaction was started by adding 2 drops of 2,6-lutidine. The reaction was held at a temperature of 70° C. overnight (19 hrs). The reaction vessel was placed in the refrigerator and the cold EtOAc was decanted from the solid reaction products. The reaction products were then rinsed with cold EtOAc (1 mL). The crude product, p-nitrosuccinanilic acid, was obtained by removing some reaction co-products using thin layer chromatography (TLC). The solid reaction products were dissolved in N,N-dimethylformamide (DMF) and spotted on Kieselgel 60 F254 HPTLC plates containing a concentration zone (EM Science No. 13728). The plates were developed using solvent system chloroform ($CHCl_3$):EtOAc:methanol (MeOH):formic acid, 86:10:4:1%. The desired product remained at the origin. The origin band was scraped and eluted with DMF. The DMF was removed with a stream of argon gas. The sample was dissolved in 30% MeOH/$H_2O$ and made slightly basic using a solution of sodium hydroxide (4 N). The product was collected from HPLC using a 15 cm×4.6 mm, 5 µm, Supelcosil LC-ABZ column with a solvent system of 30% MeOH at a flow rate of 1 mL/min., at 254 nm; sodium p-nitrosuccinanilate ($C_{10}H_9N_2NaO_5$) in a yield of 59%. Accurate mass measurement was observed by Fast Atom Bombardment on the double sodium ion at 283.0326 (calculated for $C_{10}H_9N_2Na_2O_5^+$, 283.03069 (Δ1.91 ppm)).

EXAMPLE 2

Hybridoma Production

Immunization Protocol and Hybridoma Production.

Animal immunization and hybridoma production substantially followed the protocols described in Stanker et al. (U.S. Pat. No. 5,908,781), the contents of which are incorporated by reference herein.

Antibodies and ELISA Methods.

A standard indirect ELISA method in which nicarbazin was immobilized on 96-well microtiter plates was used to evaluate the hybridomas for antibody production. The same antigen (nicarbazin) coated plates were used for all screening procedures. Except as described below, the assays (both indirect ELISA and competitive indirect ELISA) were performed substantially as described in Stanker et al. (U.S. Pat. No. 5,908,781).

Assay buffer used in the assays was prepared in two parts as follows. In part A, the following ingredients were added to 950 mL of R.O. water: 11.44 g Tris-HCl (TRIZMA Hydrochloride, tris[hydroxymethyl]-aminomethane hydrochloride) (Sigma No. T-3253), 3.32 g TRIZM Base, tris[hydroxymethul]aminomethane (Sigma No. T-8524), and 8.76 g NaCl (Sigma No. S-9888). The pH of this solution was adjusted to 7.75 (if necessary), and the volume adjusted to 1 liter. In solution part B, 0.5 mL Tween 20 and 1 g NFDM (non-fat dry milk) were added to 95 mL R.O. water or distilled water. To prepare Assay Buffer, at the time of use, add 995 mL Part A and 5 mL Part B.

The 96-well plates were coated with antigen coating procedure: A solution of nicarbazin (1.41 µg/mL) in 50% MeOH and 50% Part A of the Assay Buffer in 0.006% Tween 20 was made so that it had a concentration of 1 µg/mL of carbanilide. 100 µL of this solution was placed in each well of the 96-well plates and kept overnight in the fridge. The plates were washed five times with Tween 20 (0.05%) in R.O. water. The wells were blocked using 300 µL of a 3% solution of non-fat dry milk (NFDM) in phosphate buffered saline at pH 9 for 1 hr. The NFDM solution was removed and the wells washed three times with 0.05% Tween 20.

Following the fusion, the fused cells were distributed into 30 96-well plates (for a total of 2880 wells). The initial screen was performed in a standard indirect ELISA. 100 µL of the media from each well of the 30 96-well plates was placed into a nicarbazin coated well and incubated at 37° C. for 1 hr. The wells were washed five times with 0.05% Tween 20. 100 µL of the second antibody (anti-mouse IgG (whole molecule) peroxidase conjugate) at a dilution of 1:500 in Assay Buffer plus 2% NFDM was placed into each well and incubated at 37° C. for 1 hr. The second antibody solution was removed and the plates were washed five times with 0.05% Tween 20. K-blue substrate (50 µL) was added to each well, and after 30 min. the positive wells were marked. Each of the marked wells, or picks was transferred from the original 30 96-well plates to 24-well macrophage coated plates to allow the cells to grow and expand. This was done to obtain enough media to do a titration of the antibody and then a competition with a standard solution of nicarbazin.

Titrations of picks from the 24-well plates were accomplished in a solution of 3% DMF and 10% acetonitrile (ACN). Using nicarbazin-coated plates, media (174 µL) from each of the picks in the 24-well plates was placed in a well in row B of the nicarbazin coated plates. 100 µL of a solution of 3% DMF and 10% ACN in Assay Buffer was placed in all wells of row A (negative control) and in the wells of rows C–H. 26 µL of the solvent mix (23.1% DMF and 76.9% ACN) was added to each well in row B. The addition made the final concentration of the media become 3% DMF and 10% ACN. Row B was diluted 1:2 down the plate, and the assay was completed as normal. The plate was incubated at 37° C. for 1 hr., and washed five times with 0.05% Tween 20. The second antibody (100 µL) was added to all wells and incubated at 37° C. for 1 hr., and washed five times with 0.05% Tween 20. K-blue (100 µL) was added to all wells and incubated for 30 min. at room temp. The reaction was stopped by using 2N $H_2SO_4$ (50 μL). The plates were read at 450 nm.

The resultant titration information was the basis for the proper dilution to be made of the media from each well in the 24-well plates prior to running competitions of the media from these wells with a standard solution of nicarbazin.

The cells which were positive in the initial screening and expanded were analyzed by competitive indirect ELISA (ciELISA) as described below for inhibition of antibody binding in the presence of free (unconjugated) nicarbazin (containing free DNC) on nicarbazin coated antigen plates.

The media from each of the 24-well plates was diluted according to the titration data above so that the Absorbance at 450 nm of the final solution would be between 0.4 and 0.45.

In column 1 of a nicarbazin coated 96-well plate, 100 μL of a solution of 3% DMF and 10% ACN in Assay Buffer was placed in each well as the negative control. In each well of column 3 was placed 100 μL of Assay Buffer. In each well of column 4–12 was placed 100 μL of 6% DMF and 20% ACN in Assay Buffer. 200 μL of the nicarbazin standard (in a solution of 12% DMF, 40% ACN and 0.1% Tween 20 in Part A Assay Buffer) was placed in each well of column 2. Column 2 through Column 10 was diluted 1:2 across the 96-well plate. This assured that all wells within Column 3 through Column 12 had a concentration of 6% DMF and 20% ACN in Assay Buffer.

After all dilutions were made, 100 μL of the media at the correct dilution (based on the above titrations) from the 24-well plates was layered on top of each well (from column 2 to column 12). Therefore, each row contained diluted media from one well of a 24-well plate. The resultant organic solvent concentration in each well from Column 3 to Column 12 was 3% DMF and 10% ACN in Assay Buffer. However, the final concentration of organic solvent in Column 2 was 6% DMF and 20% ACN. This was normally too high of an organic solvent concentration for the ELISA to work properly, and therefore, the data from Column 2 was discarded. The 96-well plate was incubated at 37° C. for 1 hr., and then washed five times with 0.05% Tween 20. The second antibody (100 μL) was added to all wells and incubated at 37° C. for 1 hr., and washed five times with 0.05% Tween 20. K-blue (100 μL) was added to all wells and incubated for 30 min. at room temp. The reaction was stopped by using 2N $H_2SO_4$ (50 μL). The plates were read at 450 nm. The data was plotted as % Inhibition vs. quantity of nicarbazin (ng/well). The results for three of the antibodies are shown in FIG. 1. The monoclonal antibodies detected nicarbazin from 652 to about 2194 ng at their $IC_{50}$. The lowest level of detection ranged from about 206 to about 471 ng at the $IC_{35}$ of antibody B, and $IC_{20}$ of A, respectively, in the competitive inhibition ELISA.

Cell cultures which produced antibodies whose binding was inhibitable by free DNC were subcloned, resulting in the establishment of ten stable monoclonal cell lines secreting anti-DNC antibodies. These hybridoma cell lines were designated as follows:

PNA-S2 6/3-56(2)-3-1-5,
PNA-S2 6/3-56(1)-1-5-1,
PNA-S2 6/3-56(1)-1-5-2,
PNA-S2 6/3-56(1)-1-10-4,
PNA-S2 6/3-56(1)-1-10-5,
PNA-S3 7/23-81-1,
PNA-S3 7/23-81-3,
PNA-S3 7/23-81-4,
PNA-S3 7/23-81-5, and
PNA-S3 7/23-81-6.

The PNA-S3 7/23-81-3 and PNA-S3 7/23-81-4 cell lines were selected and subcloned one additional time resulting in the establishment of two stable hybridoma cell lines secreting anti-DNC antibodies, designated PNA-S3 7/23-81-3-2 (Nic 6) and PNA-S3 7/23-81-4-2 (Nic 7), respectively. These final two hybridoma cell lines have been deposited under the Budapest Treaty in the American Type Culture Collection (ATCC), 10801 University Blvd., Manassas, Va., 20110-2209, USA, on Nov. 1, 2000, and have been assigned accession nos. ATCC PTA-2647 and ATCC PTA-2648, respectively.

EXAMPLE 3

Production of Hapten Used for Plate Coating: Synthetic Method for p-nitro-cis-1,2-cyclohexanedicarboxanilic Acid.

The desired product was made by dissolving p-nitroaniline (0.1 g, 0.724 mmol) and cis-1,2-cyclohexanedicarboxylic anhydride (0.446 g, 2.896 mmol) in EtOAc (4 mL). Addition of 2 drops of 2,6-lutidine started the reaction, and it was held at a temperature of 70° C. overnight (19 hrs). The reaction vessel was cooled to 4° C. and the solvent was decanted from the solid products. The products were rinsed with cold EtOAc (1 mL). A crude product was obtained by removing some impurities by TLC using Kieselgel 60 $F_{254}$ HPTLC plates using the solvent system $CHCl_3$:EtOAc:MeOH:formic acid, 86:10:4:1%. Following TLC, the material was made basic using sodium hydroxide (4N). The final product was separated and collected from HPLC using a 15 cm×4.6 mm, 5 μm, Supelcosil LC-ABZ column with a solvent system of 30% MeOH at a flow rate of 1 mL/min., at 254 nm. Sodium p-nitro-cis-1,2-cyclohexanedicarboxanilate (PNA-C) ($C_{14}H_{15}N_2NaO_5$) was obtained in a yield of 56%. To convert the product to the acid form, this material was extracted from pH 3.00 biphthalate buffer with dichloromethane and dried with sodium sulfate. Accurate mass measurement was obtained by electrospray MS on a PE-Sciex QSTAR Pulsar mass spectrometer of the M-H- ion at m/z 291.0978 (calculated for $C_{14}H_{15}N_2O_5-$, 291.098097 (Δ 0.297 ppm)).

BSA Conjugate of Hapten Used for Plate Coating.

The plate coating antigen was produced by dissolving Sulfo-NHS (15.4 mg, 0.071 mmol) in dry DMF (1 mL), and combined with a solution of Hapten-2 (22.6 mg, 0.072 mmol) in dry DMF (0.25 mL). To this solution was added DCC (14.1 mg, 0.068 mmol) and dry DMF for a final volume of 2.5 mL DMF. After stirring for 2 hrs. at room temperature, the reaction mixture was added to a solution of BSA (43.1 mg) in $H_2O$ (6 mL, pH 8.5). During the addition, NaOH (0.1 N) was used to keep the pH~8.5. The reaction mixture was stirred overnight at room temperature. The mixture was then dialyzed against a solution of 20% DMF and three times against $H_2O$ at 4° C. using Spectra/Por 4 dialysis membrane tubing, MWCO 12-14,000.

It is understood that the foregoing detailed description is given merely by way of illustration and that modifications and variations may be made therein without departing from the spirit and scope of the invention.

We claim:

1. A hybridoma cell line which produces and secretes monoclonal antibodies which selectively bind to 4,4'-dinitrocarbanilide, which is produced using an immunization preparation comprising p-nitroaniline conjugated to an immunogenic carrier.

2. The hybridoma cell line of claim 1 wherein said p-nitroaniline is conjugated to said immunogenic carrier through the amine group of said p-nitroaniline.

3. The hybridoma cell line of claim 2 wherein said immunogenic carrier is a protein.

4. The hybridoma cell line of claim 2 wherein said immunization preparation further comprises a crosslinking agent between said immunogenic carrier and said amine group of said p-nitroaniline.

5. The hybridoma cell line of claim 4 wherein said crosslinking agent is selected from the group consisting of dicarboxylic acids and amino acids.

6. The hybridoma cell line of claim 1, wherein said cell line is selected from the group consisting of ATCC PTA-2647 and ATCC PTA-2648.

7. A monoclonal antibody produced by the hybridoma cell line of claim 1.

8. A monoclonal antibody produced by the hybridoma cell line of claim 2.

9. A monoclonal antibody produced by the hybridoma cell line of claim 4.

10. A monoclonal antibody produced by the hybridoma cell line of claim 6.

11. A method for detecting 4,4'-dinitrocarbanilide or nicarbazin in a biological sample comprising:
   (a) providing a sample of biological material;
   (b) subjecting said sample to an immunosorbent assay using a monoclonal antibody which selectively binds to 4,4'-dinitrocarbanilide and which is produced by the cell line of claim 1, said monoclonal antibody forming an immunocomplex with 4,4'-dinitrocarbanilide or nicarbazin when said 4,4'-dinitrocarbanilide or said nicarbazin are present and
   (c) detecting said immunocomplex, wherein the detection of said immunocomplex indicates the presence of 4,4'-dinitrocarbanilide or nicarbazin in said biological sample.

12. The method of claim 11 wherein said cell line is selected from the group consisting of ATCC PTA-2647 and ATCC PTA-2648.

13. The method of claim 11 wherein said sample is selected from the group consisting of feeds, animal tissue, and animal fluids.

14. The method of claim 13 wherein said sample is tissue from poultry.

15. The method of claim 11 wherein said immunosorbent assay comprises:
   (a) providing a solid substrate having 4,4'-dinitrocarbanilide or nicarbazin bound thereto;
   (b) contacting said sample with said solid substrate and said monoclonal antibody;
   (c) washing said support;
   (d) detecting any monoclonal antibody bound to said support; and
   (e) determine the presence of 4,4'-dinitrocarbanilide or nicarbazin in said sample.

16. The method of claim 11 wherein said immunosorbent assay is a competitive inhibition assay comprising:
   (a) providing a solid substrate having p-nitroaniline conjugated to a carrier bound thereto;
   (b) contacting said sample with said solid substrate and said monoclonal antibody at pH of approximately 7.4, wherein said monoclonal antibody may bind with either said p-nitroaniline or with 4,4'-dinitrocarbanilide or nicarbazin in said sample;
   (c) washing said support;
   (d) detecting any monoclonal antibody bound to said p-nitroaniline on said support; and
   (e) determining the presence of 4,4'-dinitrocarbanilide or nicarbazin in said sample.

17. A kit for the detection or quantification of the 4,4'-dinitrocarbanilide or nicarbazin in a biological sample comprising a monoclonal antibody which selectively binds to 4,4'-dinitrocarbanilide and which is produced by the hybridoma cell line of claim 1.

18. The kit of claim 16 wherein said cell line is selected from the group consisting of ATCC PTA-2647 and ATCC PTA-2648.

* * * * *